(12) United States Patent
Livneh et al.

(10) Patent No.: US 9,662,024 B2
(45) Date of Patent: May 30, 2017

(54) BIOMEDICAL ELECTRODE ASSEMBLY

(71) Applicant: NEW N.I. MEDICAL (2011) LTD., Kfar Mallal (IL)

(72) Inventors: Aviad Livneh, Savion (IL); Evgeny Granov, Ra'anana (IL); Igor Granov, Ra'anana (IL)

(73) Assignee: NEW N.I. MEDICAL (2011) LTD., Kfar Mallal (IL)

( * ) Notice: Subject to any disclaimer, the term of this patent is extended or adjusted under 35 U.S.C. 154(b) by 219 days.

(21) Appl. No.: 14/376,861

(22) PCT Filed: Feb. 4, 2013

(86) PCT No.: PCT/IL2013/050105
§ 371 (c)(1),
(2) Date: Aug. 6, 2014

(87) PCT Pub. No.: WO2013/121415
PCT Pub. Date: Aug. 22, 2013

(65) Prior Publication Data
US 2014/0378802 A1    Dec. 25, 2014

Related U.S. Application Data

(60) Provisional application No. 61/601,295, filed on Feb. 21, 2012.

(30) Foreign Application Priority Data

Feb. 16, 2012  (IL) .......................................... 218146

(51) Int. Cl.
*A61B 5/04*    (2006.01)
*A61B 5/053*    (2006.01)
(Continued)

(52) U.S. Cl.
CPC ............ *A61B 5/04* (2013.01); *A61B 5/04085* (2013.01); *A61B 5/0492* (2013.01); *A61B 5/053* (2013.01);
(Continued)

(58) Field of Classification Search
CPC . A61B 5/04001; A61B 5/0408; A61B 5/0416; A61B 5/04085; A61B 5/0492; A61B 5/053; A61B 5/0531
See application file for complete search history.

(56) References Cited

U.S. PATENT DOCUMENTS 4,072,388 A * 2/1978 Dunn .................... A61B 5/0416
439/268
4,178,052 A * 12/1979 Ekbom .................. H01R 11/22
439/268
(Continued)

FOREIGN PATENT DOCUMENTS

CN       101385203       3/2009
WO       2005099606      10/2005

OTHER PUBLICATIONS

Search Report for Chinese Patent Application No. 2013800094731, mailed Dec. 3, 2015.

*Primary Examiner* — Lee S Cohen
(74) *Attorney, Agent, or Firm* — Wiggin and Dana LLP; Gregory S. Rosenblatt; Andrew D. Bochner

(57) ABSTRACT

A biomedical electrode structure is presented. The electrode structure comprises a contact member having a tissue interfacing face for contacting a tissue surface, and an opposite electrical coupling face; at least a first electrically conductive surface disposed within said tissue interfacing face, and being configured to electrically couple to a portion of the contacted tissue; and at least two electrical connectors mounted in a spaced apart relationship on said electrical coupling face and electrically coupled to different regions of
(Continued)

said electrically conductive surface for allowing measurement of at least one electrical property of at least a portion of said at least first electrically conductive surface residing therebetween.

17 Claims, 5 Drawing Sheets

(51) Int. Cl.
    *A61B 5/0492*     (2006.01)
    *A61B 5/0408*     (2006.01)
    *G01R 35/00*     (2006.01)
    *H01R 13/627*     (2006.01)
    *A61B 5/0416*     (2006.01)

(52) U.S. Cl.
    CPC .......... *A61B 5/0531* (2013.01); *G01R 35/005* (2013.01); *H01R 13/6273* (2013.01); *A61B 5/0416* (2013.01); *A61B 2560/0223* (2013.01); *A61B 2562/0209* (2013.01)

(56) References Cited

U.S. PATENT DOCUMENTS

| | | | |
|---|---|---|---|
| 5,372,125 A | | 12/1994 | Lyons |
| 6,134,480 A | * | 10/2000 | Minogue .............. A61N 1/0452 600/391 |
| 6,415,170 B1 | | 7/2002 | Loutis et al. |
| 6,636,754 B1 | | 10/2003 | Baura et al. |
| 7,270,580 B2 | | 9/2007 | Bradley et al. |
| 7,771,419 B2 | | 8/2010 | Carmel et al. |
| 9,144,387 B2 | * | 9/2015 | Ko .......................... A61B 5/04 |
| 2006/0068649 A1 | | 3/2006 | Silber |
| 2007/0118031 A1 | | 5/2007 | Silber |
| 2011/0251817 A1 | | 10/2011 | Burns et al. |

* cited by examiner

BIOMEDICAL ELECTRODE ASSEMBLY

CROSS REFERENCE TO RELATED APPLICATIONS

This application is a United States national-phase application pursuant to 35 U.S.C. §371, claiming benefit of international PCT Application No. PCT/IL2013/050105, titled "BIOMEDICAL ELECTRODE ASSEMBLY" that was filed Feb. 4, 2013, which claims the benefit of U.S. Provisional Patent Application No. 61/601,295, that was filed Feb. 21, 2012, and Israeli Patent Application No. 218146, filed Feb. 16, 2012. The disclosures of application serial numbers PCT/IL2013/050105, 61/601,295, and 218146 are incorporated by reference herein in their entirety.

FIELD OF THE INVENTION

This invention relates to a biomedical electrode assembly for electrically contacting a tissue.

BACKGROUND OF THE INVENTION

Biometric electrodes are used in various clinical and biomedical applications for electrically interfacing between examined tissue and monitoring instrumentation. Such biometric electrodes are usually comprised from an adhesive patch having an adhering side (also referred to herein as tissue interfacing face) comprising an electrically conductive surface, and an electrical connector mounted on the other side (also referred to herein as electrically coupling face) of the adhesive patch and electrically coupled to the electrically conductive surface. Electrically conducting wires equipped with mating connectors are used to connect to the electrode and establish electrical connection between the electrically conductive surfaces of the biomedical electrodes and the instruments used for sensing and/or applying electrical signals therethrough.

For example, in electrocardiography (ECG) biometric electrodes attached to the skin over the chest area of a patient are used for sensing electrical signals of the heart (also known as passive electrodes), while in impedance cardiography (ICG) biomedical electrodes are also used to transfer electrical signals to the tissue and sense responsive electrical signals from the tissue contacted by an electrically conductive surface of an electrode (also known as active electrodes).

Design considerations of active electrodes used to apply electrical signals to a contacted tissue usually concentrate on obtaining good electrical contact between the electrically conductive surface of the electrode and the contacted tissue while neglecting patients' discomfort due to the applied electrical signals. There have been some attempts to alleviate patient discomfort associated with the use of biomedical electrodes. For example, U.S. Pat. No. 7,771,419 describes various techniques to distribute the electrical currents applied by the electrode by using an electrode mechanically and electrically divided into multiple metallic electrodes to provide a resistive-capacitive or resistive-inductive voltage divider.

A biomedical electrode is described in U.S. Pat. No. 5,372,125 which is made of a thin flat and flexible material and includes a die-cut patch having a non-conductive adhesive coating applied on one side of the patch, a foundation component formed into four integral functional areas, a conductive component made up of an electrically conductive material with three contiguous portions, and a conductive media.

U.S. Pat. No. 6,415,170 described a biomedical electrode comprising a connector stud anchored in a patch of adhesive-coated backing material used to secure the electrode to the skin of a patient, the connector stud is located in a pierced opening in the backing material and has a head portion to which an electrical lead of an electromedical monitoring/diagnostic system can be attached, and an electrode plate which placed in electrical communication with the skin of the patient.

In WO 2005/099606 there is described a biomedical return electrode for electrosurgery or radiofrequency (RF). The biomedical electrode in this publication comprise a biomedical electrode pad, an electrode conductor for receiving electrical energy from tissue via a return path, and a thermochromic liquid crystal (TLC) layer coupled to the conductor, where the TLC layer is configured to change its colour at one or more sites dependent upon the conductor temperature at each site.

General Description

The present invention relates to a novel biomedical electrode assembly configured and operable to perform an actual measurement mode, as well as a testing mode suitable for testing the electrode condition which may be used to determine whether the electrode is in an acceptable condition for use in a medical procedure, and/or to generate calibrating data usable for calibrating electric signals measured using the electrode assembly.

With regard to the test mode, the following should be understood. In the conventional ECG and ICG applications it is usually assumed that the skin-electrode interface (i.e., the electrical properties of the connection obtained between the electrically conductive surface of the electrode and the contacted tissue) is acceptably good and that the electrically conductive surface of the electrodes is in good functioning condition. However, these conditions cannot always be met, and actually tend to degrade over time. In fact, the conditions of electrically conductive electrodes employing moistening materials (e.g., Hydrogel) for improving the tissue-electrode interface may degrade during continuous use of the electrode, particularly due to lose of moisture and reduced concentrations of electrically conductive minerals (e.g., silver) at the interface area.

For example, gel based electrodes, which tend to dehydrate over time, have specific shelf life terms (e.g., 18 months) after which they are expired and should not be used. In addition, if the unpacked electrodes are not properly maintained (e.g., the electrodes are exposed to direct sunlight or high temperature conditions), or in attempts to reuse the unpacked electrodes, the effectiveness of the electrodes may degrade and affect the signals measured or applied therewith. These problems are particularly relevant to home or mobile medical appliances intended for in-home use, wherein the electrodes may be transported in vehicles to user's houses. The environmental conditions in vehicles are usually not suitable (e.g., high temperature, direct sunlight, dryness) for storing such gel based electrodes, and may substantially shorten their life-cycle.

It is therefore desirous to allow testing and verifying the electrode condition (e.g., quality of the gel used in the electrode and/or presence of electrically conducting ingredients therein), while conventional monitoring instruments and the electrodes used nowadays are incapable of providing the practitioner with indications about the reliability of the used electrodes, as well as with capabilities to evaluate these conditions.

The biomedical electrode assembly of the present invention is configured to be electrically coupled to a skin tissue, whereby it may be operated in an active mode for applying electrical signals to the contacted tissue, or in a sensing mode for sensing electrical signals propagating in the contacted tissue, for determining one or more physiological parameters (e.g., patient's hemodynamics).

The electrode assembly of the present invention in some of its embodiments includes a contact member having a tissue interfacing face, by which it is brought in contact with the skin, and an electrical coupling face, used for electrically coupling the electrode to equipment (e.g., monitoring equipment) suitable for measuring and/or applying electrical signals therewith. In some preferred embodiments of the present invention the biomedical electrode includes an elongated electrically conductive surface (also referred to herein as a main electrode) longitudinally disposed along a surface area on the tissue interfacing face of the contact member.

The use of an electrical conductive surface having an elongated shape advantageously increases the length of the contact area, and thereby improves the tissue-electrode interface. Also, the use of an elongated electrical conductive surface can provide for improving the homogeneity of the applied electrical currents in the contacted tissue by arranging such elongated electrically conductive surface on the tissue interfacing face of the contact member to cause the electrical currents applied to the contacted tissue to propagate therein in a direction substantially perpendicular to the elongated electrically conductive surface of the electrode. Furthermore, using an elongated electrically conductive surface provides for reducing the density of the electrical current applied to the tissue. In this way, patient's discomfort which may occur due to the transmission of electrical currents to the tissue may be alleviated or even prevented.

The electrode assembly may comprise at least two spaced apart connectors disposed on the electrical coupling face of the contact member and electrically coupled to the elongated electrically conductive surface of the electrode assembly. The spaced apart connectors may be configured and operable to connect to at least two mating connectors, to thereby obtain mechanical and electrical connection therewith. With this design the biomedical electrode assembly of the present invention may be used to provide homogenous distribution of electrical currents transferred to the contacted tissue through the electrical conductive surface of the electrode (e.g., due to applied electrical signals) and alleviate patient discomfort which may be caused by the applied electrical currents.

In the testing mode, the biomedical electrode may be used to measure electrical properties of the electrically conductive surface of the electrode itself and thereby enable to test and verify the condition of the electrically conductive surface of the electrode.

For example, the electrically conductive surface of the electrode of the present invention may include an electrically conductive gel medium. For effective measurements, the gel medium should satisfy a certain conditions of humidity and a certain concentration of electrically conducting materials (e.g., salts, and/or other minerals). Such types of electrodes typically suffer from the fact that gel becomes dry over time and that its electrical conductivity properties degrade over time (e.g., due to inadequate maintenance conditions), which should be identified prior to (or during) the use of the electrode assembly, otherwise meaningful measurements might not be performed. Furthermore, the condition of the electrically conductive surface of the electrode may change during a prolonged usage, and also the electrical properties of the skin-electrode interface may introduce interferences (noise) in the electrical signals sensed, or applied, via the electrode.

Calibrating data computed based on electrical properties of the electrically conductive surface measured in the testing mode may be further used to adjust electrical signals sensed, or applied, via the electrode assembly to reduce or eliminate interfering effects, such as noise, which may be introduced during normal use of the electrode.

Thus, in possible embodiments of the present invention a calibration stage may be carried out, before or during, the use of the biomedical electrodes of the present invention for actual measurements on a tissue. In the calibration stage, electrical properties (e.g., electrical resistance or conductivity) of the electrically conductive surface of the electrode are measured, enabling to use such measured data to determine whether the electrode is in an acceptable condition for use in a medical procedure, and/or to generate the calibrating data.

At least one of the at least two connectors mounted on the electrically coupling face may be used to transfer electrical signals (charges), received via the mating connector to which it is connected, to the electrically conductive surface of the biomedical electrode. In the testing mode, at least one other connector of the at least two connectors may be used for sensing electrical currents propagating in the electrically conductive surface of the electrode assembly e.g., via a mating connector to which the at least one other connector is connected, for measuring at least one electrical property of the electrically conductive surface of the electrode.

Advantageously, when operated in the active mode two or more connectors may be used to apply electric signals to the contacted tissue via the electrically conductive surface of the electrode.

In some embodiments of the present invention the contact member includes an additional electrically conductive surface (also referred to herein as additional electrode) disposed spaced apart from the elongated electrode on the tissue interfacing face of the contact member and configured and operable to contact another piece of tissue of the patient. An at least one additional connector, electrically coupled to the additional electrically conducting surface, may be disposed on the electric coupling face of the contact member for establishing electrical and mechanical connection with an additional mating connector.

Therefore, some embodiments of the present invention provide an electrode assembly having a main electrically conductive surface disposed on a surface area of the contact member, and an additional electrically conductive surface disposed spaced apart on a surface area of the contact member. These embodiments of the electrode assembly of the present invention permit operating the electrode assembly in a mixed mode, wherein the main electrically conductive surface of the electrode assembly is used to apply electrical signals to the contacted tissue, while the additional electrically conductive surface of the electrode assembly is used to sense electrical signals propagating in the contacted skin in response to the electrical signals applied.

The main electrically conductive surface is an elongated surface electrically coupled to at least two electrical connectors, as described hereinabove and hereinbelow. The additional electrically conductive surface may have a circular or polygonal shape or any other suitable shape, electrically coupled to one or more additional electrical connectors. Optionally, the additional electrically conductive surface is also an elongated surface having two or more additional spaced apart connectors, as described hereinabove and hereinbelow.

In possible embodiments of the present invention the main and the additional electrically conductive surfaces may be configured to allow operating the electrode assembly of the present invention in a testing mode usable for testing their conditions. Optionally, the additional electrically conductive surface is configured as an elongated surface disposed on the tissue interfacing face of the contact member, spaced apart and in parallel to the main electrically conductive surface. Arranging the elongated main and additional electrically conductive surfaces in parallel causes the electrical currents to propagate in the contacted tissue in a direction substantially perpendicular to the elongated electrically conductive surfaces, which helps to evenly and homogenously distribute the electrical currents in the contacted tissue and thus alleviate or prevent patient discomfort.

The biomedical electrodes of the present invention may be operated by a measurement device configured and operable to test the electrically conductive surface(s) of the electrodes (testing mode), and after verifying that the electrodes are in acceptable operating condition, to apply and/or sense electrical signals (measuring mode) via one or more biomedical electrodes of the present invention that are electrically coupled to a tissue of a subject. In exemplary embodiments of the present invention the measurement device operates to selectively switch between the testing and measuring modes.

In the testing mode, the measurement device operates to apply electrical signals through at least one connector electrically coupled to one of the electrically conductive surfaces of the electrode, and sense electric signals propagating in the tested electrically conductive surface of the electrode via another connector electrically coupled thereto. The measurement device may then analyze the sensed electrical signals and generate data indicative of electrical properties and/or operational condition of the tested electrically conductive surface. The sensed and analyzed electrical signals may be further used to generate calibrating data usable for adjusting electrical signals sensed or applied via the electrode.

In the measurement mode, the measurement device operates to apply and/or sense electrical signals via one or more electrically conductive surfaces coupled to a skin tissue of a subject. For example, if operated in a sensing mode, the measurement device may sense electrical signals propagating in a contacted tissue via a single electrically conductive surface of an electrode assembly of the present invention. In another possible example, the measurement device may be operated in a mixed mode to apply electrical signals through one or more connectors electrically coupled to a main electrically conductive surface, and to sense electrical signals, responsive to the applied signals, via at least one connector electrically coupled to an additional electrically conductive surface. As will be explained and demonstrated hereinbelow, the main and additional electrically conductive surfaces may be disposed on two different contact members of two different electrode assemblies of the present invention, or on a single contact member of the same electrode assembly of this invention.

A connector unit, including two mating connectors may be used to connect the electrode assembly of the present invention to monitoring equipment. The mating connectors in some embodiments are shiftable between engaged state and disengaged state, such that when in their engaged states the connectors grab corresponding connecting elements, and release them when in their disengaged states. The mating connectors may be associated with two respective actuators, each actuator being configured and operable to reversibly change the state of a corresponding connector, to thereby allow the operator to attach the connector unit to the electric connectors mounted on the electrically coupling face of the contact element.

The electrode assembly of the present invention may be a type of patch-electrode or self-adhesive electrode.

There is therefore provided according to one aspect of the present invention a biomedical electrode structure comprising a contact member having a tissue interfacing face for contacting a tissue surface and an opposite electrical coupling face, at least a first electrically conductive surface disposed within said tissue interfacing face and being configured and operable to electrically couple to a portion of the contacted tissue, at least two electrical connectors mounted in a spaced apart relationship on said electrical coupling face and electrically coupled to different regions of said electrically conductive surface for allowing measurement of at least one electrical property (e.g., electrical impedance, resistance or conductivity) of at least a portion of said at least first electrically conductive surface residing therebetween.

In possible embodiments of the present invention the at least first electrically conductive surface is an elongated surface. In this configuration the at least two electrical connectors may be electrically coupled to spaced apart regions of the electrically conductive surface to permit measurement of the at least one electrical property along substantial length of the electrically conductive surface (between these regions). The length of the first electrically conductive surface may generally be in the range of 30 to 60 mm, and its width may generally be in the range of 8 to 16 mm. The electrically conductive surface may have a rectangular (e.g., having an aspect ratio generally in the range of 0.13 to 0.53, oval, polygonal, or any other suitable shape.

In possible embodiments of the present invention the biomedical electrode structure may further comprise an additional second electrically conductive surface disposed on the tissue interfacing face spaced apart from the first electrically conductive surface configured and operable to contact a different portion of the contacted tissue, and at least one additional electric connector electrically coupled to said additional electrical conductive surface. The additional electrically conductive surface may be configured and operable to sense electric signals propagating in the contacted tissue in response to electric signals applied by the at least one electrically conductive surface. Optionally, the additional electrically conductive surface is an elongated surface.

In some embodiments of the present invention the first electrically conductive surface and the second electric conductive surface are configured such that electrical currents passing in the contacted tissue due to the applied electric signals propagate in a direction substantially perpendicular to at least one of said electrically conductive surfaces.

In some applications of the present invention the electrically conductive surfaces of the biomedical electrode structure are disposed on the tissue interfacing surface substantially parallel to each other, such that the electrical currents propagating in contacted tissue residing therebetween are homogenously distributed at least along the length of the contacted tissue.

The distance between the electrical conductive surfaces of the first and second electrically conductive surfaces may generally be in the range of 30 to 60 mm.

In another aspect the present invention is directed to a method for calibrating a biomedical monitoring setup. The method comprises steps of: (i) providing at least one biomedical electrode comprising an electrically conductive surface and at least two spaced apart electrical connectors electrically coupled to the electrically conductive surface; (ii) applying electrical signals to the electrically conductive surface via at least one of the electrical connectors, (iii) measuring responsive electrical signals propagating in the electrically conductive surface via at least one other of the electrical connectors and generating data indicative of the propagating electrical signals; and (iv) analyzing the data and determining at least one electrical property of the electrically conductive surface.

In possible embodiments of the present invention the method may further comprise steps of: (v) issuing an indication whenever the determined at least one electrical property is not acceptable for carrying out the monitoring; and (vi) waiting for replacement of the at least one biomedical electrode. Optionally, steps (i) to (vi) are repeated until determining that the at least one electrical property is acceptable for carrying out the monitoring.

The method may further comprise generating calibrating data indicative of electrical signals to be applied, or of electrical signals sensed, via the electrically conductive surface, based on the at least one electrical property.

According to yet another aspect, the present invention is directed to a measurement device usable for monitoring one or more physiological parameters, and comprising an electrical monitoring unit, at least one connector configured and operable to electrically couple an electrode structure to the electrical monitoring unit via at least two electrical connectors of the electrode structure, a switching circuitry configured and operable to alter connectivity between the electrical monitoring unit and the at least one connector to provide one of the following operating modes:

a testing mode for measuring at least one electrical property of said electrode; and a monitoring mode for applying electrical signals from said electrical monitoring unit to a tissue contacted by said electrode structure or for sensing via said electrode structure electrical signals propagating in said tissue.

In some embodiments of the present invention the electrical monitoring unit comprises an electrometer and an electrical signal generator.

According to another aspect, the present invention is directed to a connector unit usable for electrically coupling monitoring equipment to an electrode structure comprising two electrical connectors. In some applications the connector unit comprises two electrically conductive latching elements shiftable between engaged and disengaged states, a housing configured to receive two electrically conductive wires and electrically couple each of said wires with a respective latch element, and two actuators movably attached to said housing, configured and operable to change the states of the latching elements between their engaged and disengaged states.

Optionally, the two electrical connectors (also referred herein as connecting elements) of the electrode may be in a form of electrically conducting studs and the latching elements may be configured and operable to embrace said studs in their engaged state.

BRIEF DESCRIPTION OF THE DRAWINGS

In order to understand the invention and to see how it may be carried out in practice, embodiments will now be described, by way of non-limiting example only, with reference to the accompanying drawings, in which same reference numerals are used to identify elements or acts with the same or similar functionality, and in which.

Figure 1:
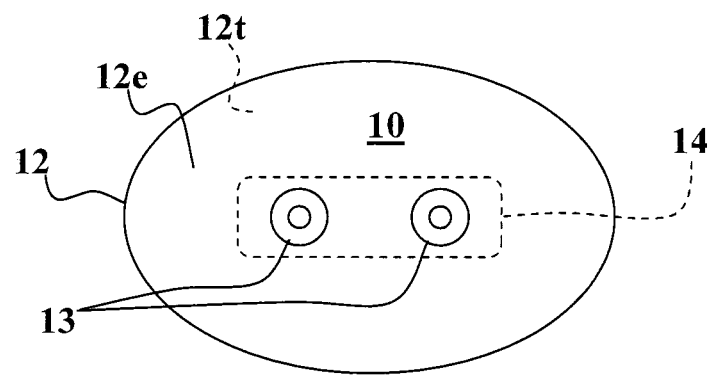
FIG. 1 shows a simplified illustration of a biomedical electrode assembly according to one possible embodiment of the present invention comprising a single electrically conductive surface.

It is noted that the embodiments exemplified in the figures are not intended to be in scale and are in diagram form to facilitate ease of understanding and description.

DETAILED DESCRIPTION OF EMBODIMENTS

The present invention generally relates to a biomedical electrode assembly comprising a contact member having a tissue interfacing face, configured to contact, and attach to a tissue surface of a patient, and an electrically coupling face. In possible embodiments of the present invention the tissue interfacing face of the contact member includes an elongated electrically conductive surface serving as a main electrode. The electrical coupling surface of the contact member includes at least two spaced apart electrical connectors electrically coupled to the elongated electrically conductive surface and configured and operable to mechanically and electrically connect the electrode assembly to monitoring equipment suitable for applying and/or sensing electric signals via the electrically conductive surface.

The electrode assembly of the present invention is configured to homogenously distribute electrical currents applied to a contacted skin tissue via the electrically conductive surface and to improve the skin-electrode interface (e.g., reduce the electrical resistance at the interface). These desirable features of the electrode assembly of the present invention contribute to minimize or eliminate patient discomfort caused due to the electrical signals applied to the contacted skin tissue of the patient. The at least two spaced apart connectors may be utilized in the active mode of operation of the electrode to apply electrical signals to the contacted tissue. More particularly, in the active mode at least two electric wires are connected to the at least two spaced apart connectors, thereby evenly distributing the applied electric signal over the length of the elongated electrically conductive surface and improving the homogeneity of the electrical current applied to the contacted skin tissue.

The electrode assembly of the present invention may be used to measure electrical properties of the electrically conductive surface of the electrode assembly in an electrode testing mode. For example, in the electrode testing mode one of the electrical connectors may be used to apply electrical signals to the electrically conductive surface, while another one of the electrical connectors may be used to measure data indicative of electrical currents passing through the electrically conductive surface responsive to the applied electric signals. The measured data may be processed to determine electrical properties of the electrically conductive surface, such as, electrical resistance or conductivity. In this way, measurements carried out with the electrode assembly of the present invention may be calibrated in accordance with determined electrical properties of the electrically conductive surface of the electrode.

The electrode assembly may further include an additional electrode disposed on the tissue interfacing face of the electrode assembly spaced apart from the main electrode. The additional electrode may be configured in any suitable geometrical shape and may be electrically coupled to at least one additional connector mounted on the electrical coupling face of the contact member.

FIG. 1 schematically illustrates a simplified embodiment of electrode assembly 10 of the present invention. In this example the electrode assembly 10 includes a contact member 12 having a tissue interfacing face 12t (a hidden surface in the view of FIG. 1—designated by a dashed line) comprising an elongated electrically conductive surface 14 (disposed on the hidden plane, shown by a dashed line), and an electrically coupling face 12e comprising two spaced apart electrical connectors, electrically coupled to the electrically conductive surface 14, generally designated by numeral reference 13. The electrical coupling of the electrical connectors 13 to the elongated electrically conductive surface 14 may be configured such that each connector is electrically coupled to a surface area of the electrically conductive surface adjacent to one of the extremities of the electrically conductive surface 14. Therefore, in order to simplify the electrical coupling, the electrical connectors 13 may be positioned on regions of the electrical coupling face 12e located over the surface area adjacent to the extremities of the electrically conductive surface 14. In this way the electrical connectors may 13 be connected directly to the electrically conductive surface 14 via one or more apertures (not shown) formed in the contact member 12.

Contact member 12 may be manufactured from any suitable electrically inert (non-conductive) material prepared in any shape suitable to accommodate the elongated electrically conductive surface 14. In some possible embodiments of the present invention the contact member 12 is made from a soft material, such as, adhesive foam, cloth or suchlike, capable of being deformed to fit and match to the curvature of the contacted tissue and provide maximal surface contact therewith. Electrically conductive surface 14 may be made from any suitable electrically conductive material capable of being pressed over the contacted tissue area and provide maximal surface of contact with the tissue. For this purpose a flexible or deformable metallic band may be used for example. In possible embodiments of the present invention the electrically conductive surface 14 comprises an electrically conducting gel composition e.g., Hydrogel 6-10% and silver enclosed by a porous membrane. The elongated electrically conductive surface 14 may be formed in a rectangular or oval shape. The electrical connectors 13 may be implemented using electrically conductive studs made from metal, such as silver for example, or from any other suitable electrically conductive material.

In some possible embodiments of the present invention the electrically conductive material is formed in a rectangular shape having a length generally in the range of 30 to 60 mm, optionally about 44 mm, and having a width generally in the range of 8 to 16 mm, optionally about 12 mm. The electrically conductive surface 14 may be disposed on the tissue interfacing face of the contact member 12 using any suitable technique, as well known in the electrode manufacture industry.

Figure 2:
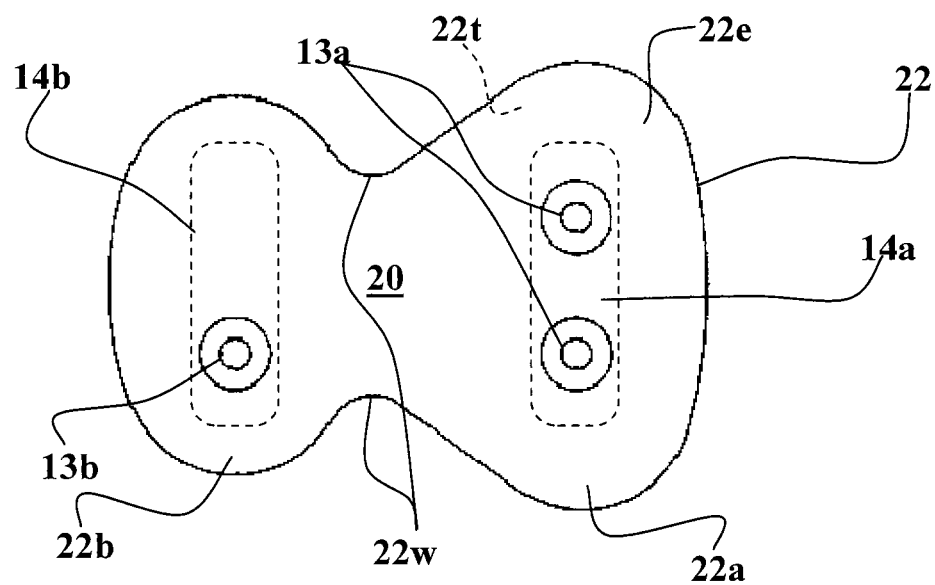
FIG. 2 shows a simplified illustration of a biomedical electrode assembly according to some embodiments of the present invention comprising a pair of electrically conductive surfaces.

With reference to FIG. 2, wherein there is shown a biomedical electrode assembly 20 according to possible embodiments of the present invention which may be used to simultaneously apply electric signals to a contacted tissue and sense responsive electric signals propagating in the contacted tissue. In this example the electrode assembly 20 comprises two electrically conducting surfaces 14a and 14b disposed in spaced apart relationship on a tissue interfacing face 22t (a hidden surface in the view of FIG. 2—designated by a dashed line) of a contact member 22. Each of electrically conductive surfaces 14a and 14b may be electrically coupled to one or more connectors mounted on the electrically coupling side of the contact member 22.

In this example, a first electrically conductive surface 14a of electrode assembly 20 is coupled to two spaced apart electrical connectors 13a disposed on regions of the electrically coupling face 22e located over regions of the tissue interfacing face 22t located near the extremities of the electrically conductive surface 14a. Though electrically conductive surface 14b is shown in FIG. 2 electrically coupled to a single electrical connector 13b, it is noted that two or more electrical connectors 13b may be used allowing testing the condition of the electrically conductive surface 14b, as described hereinabove and hereinbelow. Though the electrode assembly 20 shown in FIG. 2 exemplifies an implementation having the electrical connector 13b of electrically conductive surface 14b located over one end of the elongated electrically conductive surface 14b, the electrical connector 13b may be located over any region (e.g., ove the center) of the elongated electrically conductive surface 14b.

In the testing mode electrical signals may be applied via one of the electrical connectors 13a and data indicative of electrical properties of the electrically conductive surface 14a may be collected by sensing responsive electric signals propagating in electrically conductive surface 14a via the other electrical connector 13a. In operation, electrical signals may be applied concurrently via the two electrical connectors 13a, such that electrical charges are simultaneously applied at both ends of the electrically conductive surface 14a of the electrode. The additional electrode 14b placed parallel and spaced apart from electrically conductive surface 14a may connected via its electrical connector 13b for sensing electrical signals from the contacted tissue, such that a closed electrical circuit is obtained between the conductive surfaces 14a and 14b via the contacted tissue. With this configuration of the electrode assembly 20 the electrical charges applied by the elongated electrically conductive surface 14a propagate in the contacted tissue in a direction substantially perpendicular to the axis of the elongated electrically conductive surface 14a.

The various elements of electrode assembly 20 may be manufactured from materials and in geometrical dimensions substantially as described herein above with reference to electrode assembly 10. However, further consideration may be needed in the design of the contact member 22 which should accommodate at least two parallel spaced apart electrically conductive surfaces 14. For example, in possible embodiments of the electrode assembly 20 the gap between the electrically conductive surfaces 14a and 14b may generally be in the range of 30 to 60, optionally about 45 cm. The contact member 22 may be configured to form two flexibly connected lobes 22a and 22b, defining region areas of the contact member 22 suitable to respectively accommodate the electrically conductive surfaces 14a and 14b. The lobes 22a 22b may be connected in a waste region 22w of the contact member 22, which defines a narrow region of the contact member, that improves the flexibility and ergonomics of the electrode assembly 20 by allowing the two lobes 22a and 22b of contact member 22 to easily bend towards, or away from, each other. Optionally, one of the lobes (e.g., 22a) may have greater surface area which may serve for better anchoring one of the electrically conductive surfaces (e.g., that is used to apply the electrical signals).

Contact member 22 may further include one or more apertures and/or slits (not shown) allowing the passage therethrough, and/or anchor to the contact member, of flexible conduits or tubes used, for example, for providing medication or for carrying out treatment procedures, as may be needed.

In this way, the electric current applied to the contacted tissue is homogenously distributed in the contacted tissue via the electrically conductive surface 14a and the density of the applied electric current is evenly distributed along the length of the tissue-electrode interface. It is therefore possible with the electrode configuration of the present invention to substantially alleviate, or even prevent, any patient discomfort which may be caused due to the applied electric signals.

Figure 3:
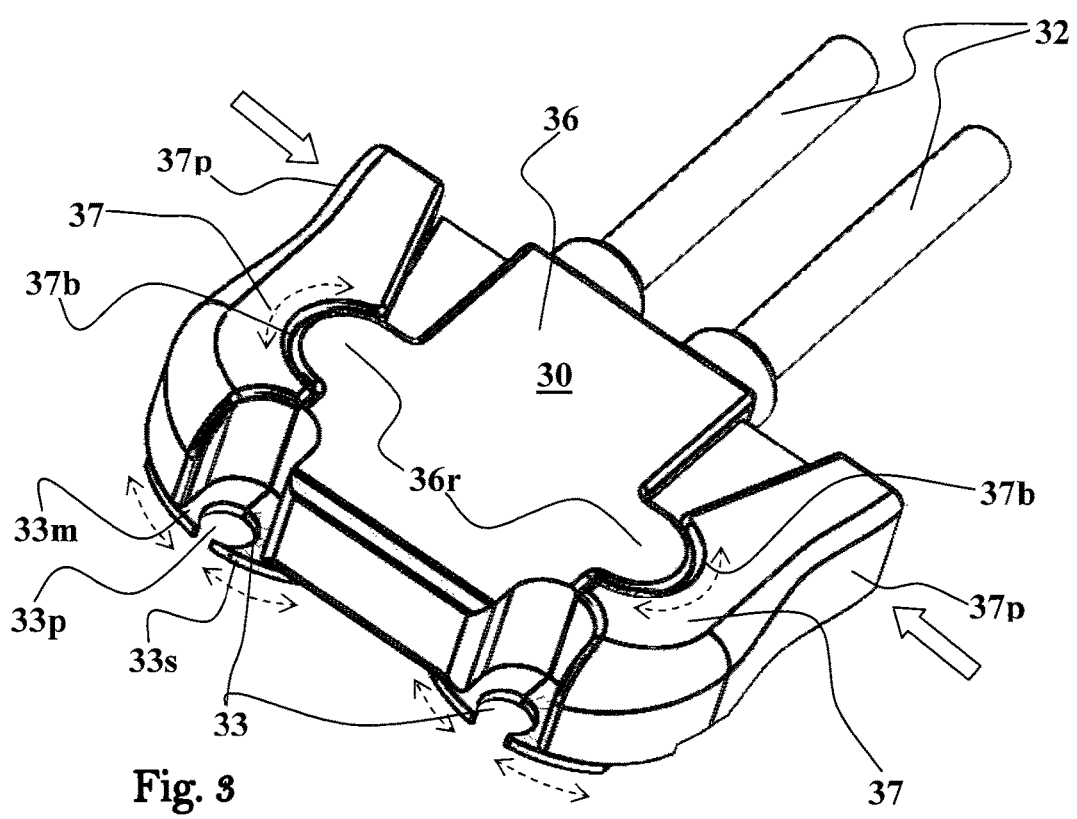
FIG. 3 is a perspective view of a connector unit of the present invention usable for conveying electrical signals to biomedical electrodes of the present invention.

FIG. 3 shows a perspective view of a connector unit design 30 suitable for electrically connecting a pair of electrically conductive wires 32 to a pair of electrical connectors (e.g., 13 or 13a) of the electrode assembly (e.g., 12 or 22) of the present invention. The connector unit 30 includes a housing 36 in which the ends of the electrically conductive wires 32 are received and electrically coupled to pair of respective electrically conductive latches 33. Housing 36 further accommodates movable actuating mechanism (not shown, e.g., hinges and springs) configured to facilitate movement of a pair of respective actuators 37 mechanically coupled to the pair of latches 33. For example, actuators 37 may be configured as depressible actuators having lever arms 3'7p mechanically coupled to latches 33 allowing changing the states of latches 33 between engaged state and disengaged states.

In one specific example lever arms 3'7p are reversibly depressible towards housing 36 and each of the latches 33 includes a stationary hook shaped member 33s and a movable hook shaped member 33m positioned in a clasping arrangement such that their hook shaped portions define a clasping opening 33p. Lever arms 3'7p may include bay portions 37b configured to movably fit and attach over respective knee elements 36r formed in opposing sides of housing 36. In this example, the user may press with two fingers the lever arms 37p towards housing 36 which will cause movable hook shaped portions 33m to move away from the stationary hook shaped portions 33s and thereby change the state of the latches 33 into their disengaged state by increasing their clasping openings 33p. The user may then place the studs of electrical connectors 13 within the clasping openings 33p of latches 33 and release the finger pressure over the lever arms 37p, thereby changing the state of the latches 33 into their engaged states, as their movable hook shaped members 33m retract back towards their respective stationary hook shaped members 33s causing clasping openings to firmly embrace the studs of the electrical connectors 13 and thereby electrically connect between the wires 32 to the studs of the electrical connectors (e.g., 13 or 13a).

Figure 4A:
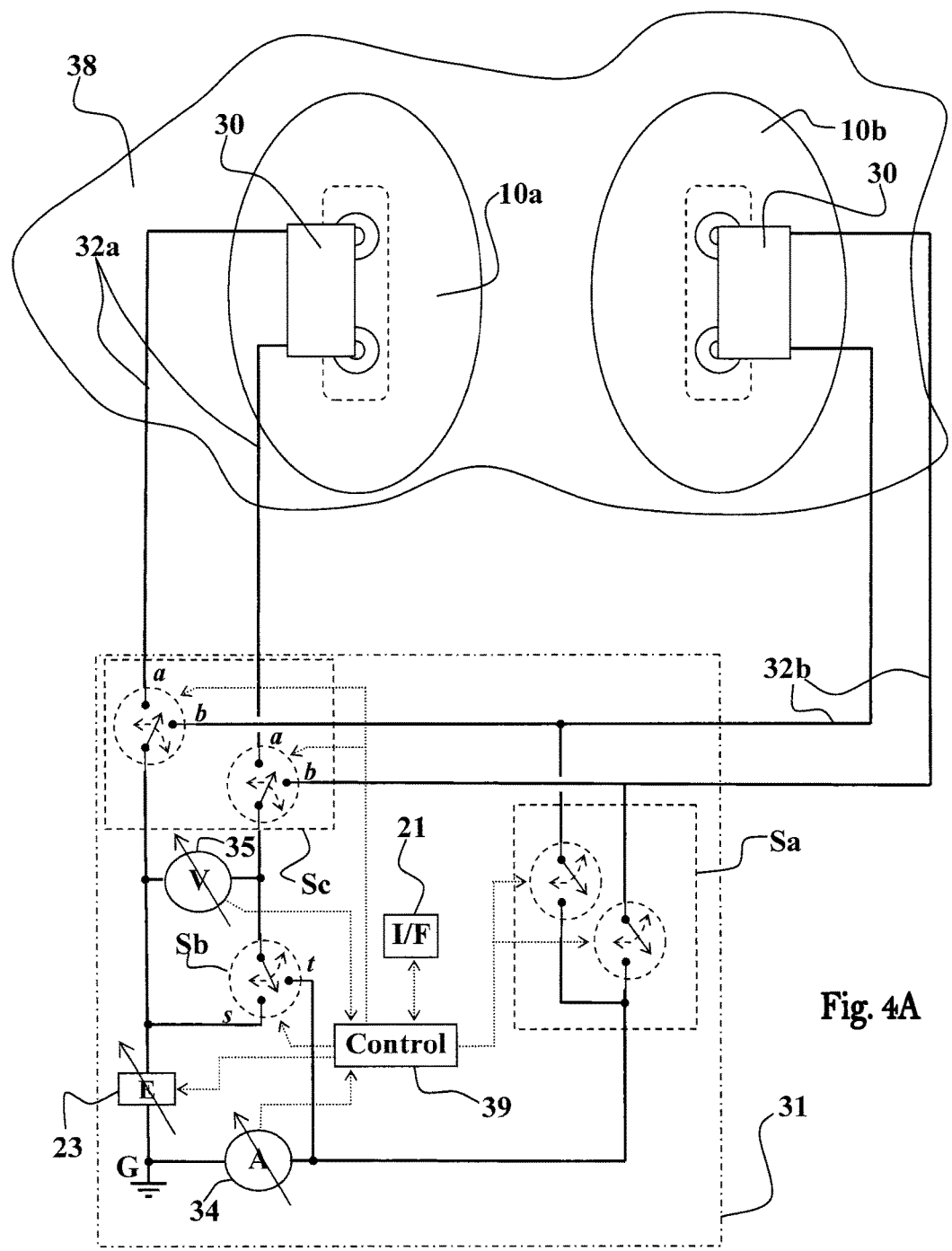
FIGS. 4A to 4C are block diagrams schematically illustrating a measurement device configured for applying and sensing electrical signals using the biomedical electrodes of the present invention, and for measuring electrical properties of the electrodes, wherein FIG. 4A exemplifies the device connected to electrodes electrically coupled to a tissue of a patient, FIG. 4B exemplifies operation of the device in the electrode testing mode, and FIG. 4C exemplifies operation of the device in a patient monitoring mode (measurement mode)

FIG. 4A exemplifies a possible apparatus 31 configured and operable to operate electrode assemblies of the present invention in their various operation modes. In this example, two electrode assemblies 10a and 10b (each similar to the electrode assembly 10 shown in FIG. 1) attached spaced apart to a piece of tissue 38 are electrically connected through wires 32a and 32b and connector units 30 to console unit 31. It is noted that the electrode assembly 20 may be similarly used in this example instead of two electrode assemblies 10a and 10b.

In an exemplary embodiments of the present invention console unit 31 includes a controllable electric signal source 23, voltmeter 35 and/or ammeter 34, switching circuitries Sa Sb Sc for altering the electrodes between their various modes of operation, a control unit 39, and optionally a user interface 21 configured and operable to interact with the user to display and receive data.

Figure 5:
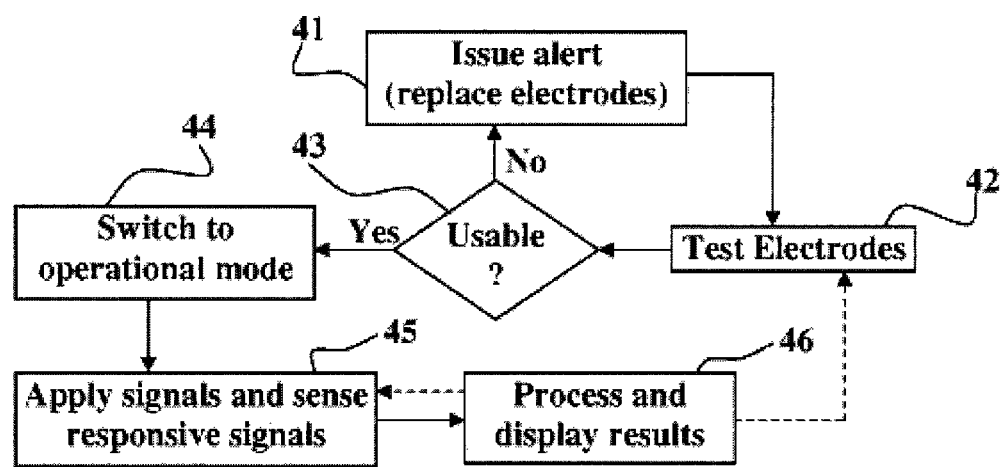
FIG. 5 is a flowchart exemplifying possible operation of the biomedical electrode of the present invention.

A simplified exemplary operation of the system illustrated in FIG. 4A will be now described with reference to the flowchart shown in FIG. 5, illustrating a possible process for operating the apparatus 31. Operation may be started in a testing step (42) wherein the conditions of the electrodes 10a and 10b is tested. In order to carry out the needed tests the control unit 39 sets the state of the switching circuitry Sb into a 'test' state (t), in which the console unit is operable to apply electric signals to the electrodes and measure the electric signal from the electrodes responsive to the passage of electrical currents through the electrically conductive surfaces of the electrodes. For example, control unit 39 may alter the state of switching circuitry Sc to choose which of the electrodes is to be tested, in state 'a' of the switching circuitry Sc a closed electrical circuit is obtained between the electric signal source 23 and the electrical connectors of electrode 10a, and in state 'b' of the switching circuitry Sc a closed electrical circuit is obtained between the electric signal source 23 and the electrical connectors of electrode 10b. The control unit 39 further alters the state of switching circuitry Sa to change the sates of its switches into an open state and thereby allow establishing a closed electrical circuit between the electric signal source 23 and the electrically conductive surface of electrode 10b.

Figure 4B:
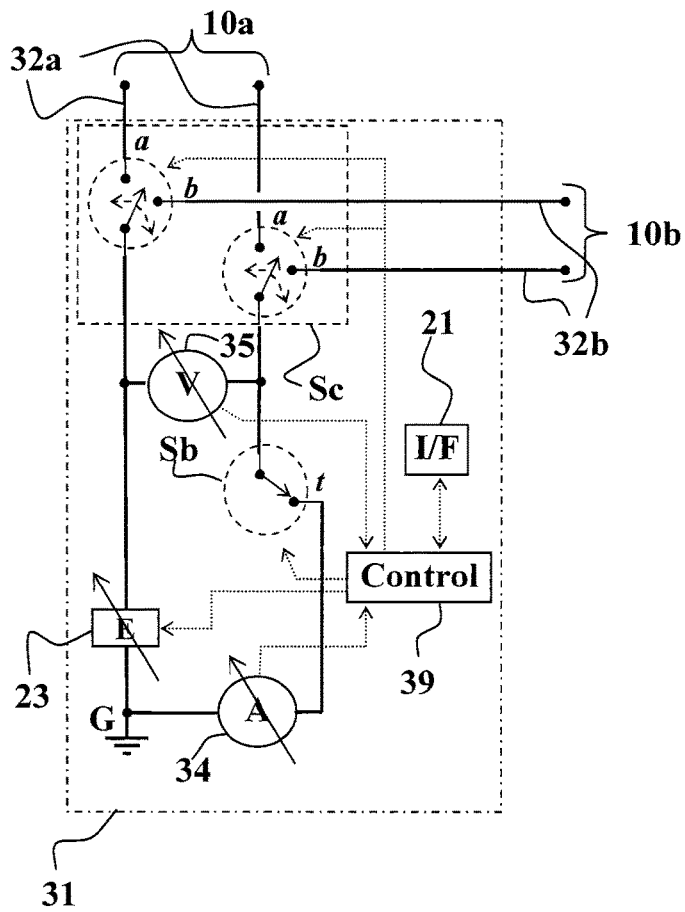

FIG. 4B exemplifies the apparatus 31 in the electrode testing state. In this state the control unit 39 may alter the switching circuitry Sc between state 'a' and 'b' to select one of the electrodes and operate the electric signal source 23 to apply electric signals having desired properties (e.g., magnitudes, waveform, frequency) over the electrical conductive surface of the selected electrode. As illustrated in FIG. 4B, control unit is also operable to receive and process current and voltage signal indications from the ammeter 34 and the voltmeter 35 in response to the electric signals applied to the electrically conductive surface of the tested electrode. The indications measured by the ammeter 34 and the voltmeter 35 may be processed by the control unit 39 to determined electrical properties (impedance, conductivity, resistance) of the electrically conductive surfaces of the electrodes.

Next, based on the electrical properties determined, the control unit 39 determines (43) if the electrodes are in operable condition. For example, based on the voltage and electrical current data indications the control unit 39 may calculate the electrical resistance of the electrically conductive surfaces of the electrodes, and then determine that the electrodes are not in acceptable condition if the determined electrical resistance is greater than some predetermined threshold value. If it is determined that one, or both, electrode(s) not in acceptable condition, than an alert is issued (41) by the control unit 39 via the user interface 21, indicating to the user which of the electrodes needs to be replaced. The alert (41) may include displaying to the user via the user interface 21 data indicative of the measured properties of the tested electrically conductive surface. The process may be halted in this stage until the user replaces the defective electrode(s) and indicates doing so via the user interface 21. Thereafter, the control is passed back to the testing step (42) to verify that the electrodes connected to the console unit 31 are in acceptable operational condition. If it is determined that the electrodes are in an acceptable operational condition, than the console unit 31 switches into an operating state as the control is passed to further steps used for applying and sensing electrical signals to/from the tissue 38.

Figure 4C:
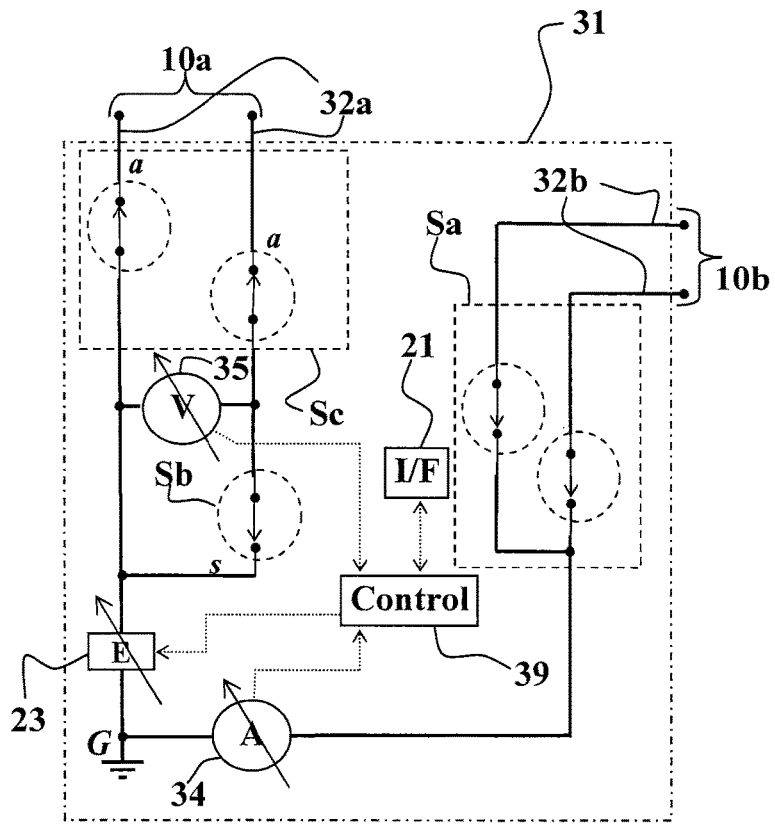

For example, in order to determine physiological parameters of the tissue 38 the control unit 39 alter the state (44) of switching circuitries Sa Sb and Sc to allow applying electrical signals via electrode 10a and sensing responsive electrical signals via electrode 10b. More particularly, as exemplified in FIG. 4C, the switches in switching circuitry Sa are changed into their closed states, thereby connecting the wires 32b connected to the electrical connectors of the electrode 10b to the ground (G) via the ammeter 34, switching circuitry Sc is changed (if so needed) into state 'a' thereby connecting the wires 32a from the electrode 10a to the voltmeter 35, and switching circuitry Sb is changed into state 's' to thereby connect both wires 32a from the electrode 10a to the output of electric signal source 23.

The control unit 39 then operates the electric signal source 23 to apply electrical signals to the contacted tissue 38 via electrode 10a, and obtains and analyze the responsive indications (45) sensed through electrode 10b via the ammeter 34. Though voltmeter 35 is not operable in this example in the tissue sensing state, additional switching circuitries may be added to alter the connectivity of the voltmeter 35 to allow using it for measuring the voltage over the electrical conductive surface of electrode 10a or 10b during the sensing stage (steps 44-46). The sensed signals are processed (46) by the control unit 39 and data indicative of the sensed signals is optionally outputted via the user interface (21). In the processing of the sensed signals the control unit 39 may combine calculated calibrating parameters determined during the electrode testing stage (42). More particularly, if it is determine during the electrode testing step that the tested electrode is usable but one or more electrical properties of the electrically conductive surface of the electrode are not within nominal operating state, control unit 39 may compute calibrating parameters accordingly to allow the calibration of signals sensed or applied via the electrode.

As demonstrated in FIG. 5, the control may be passed from step 46 back to step 45 (indicated by a dashed-arrowed line) for applying additional electrical signals and sensing responsive signals, and then processing and displaying the newly measured results by passing the control back to step 46. The process may also include one or more additional testing step(s) by passing the control from step 46 to step 42 (also indicated by a dashed-arrowed line), in order to verify during the monitoring process that the electrodes are still is acceptable operating condition, and if it is not so, to alert the user to replace the used electrode(s) with fresh electrode(s).

Control unit 39 may be include one or more processing units (e.g., CPU, MCU) and/or control logic, and one or more memory units (e.g., ROM, RAM, NVRAM, FLASH, magnetic/optic disks, or suchlike). The user interface 21 may include a display device (e.g., LCD, CRT) and one or more input devices (e.g., keyboard/keypad, mouse, or suchlike) allowing displaying to the user information, and receiving information from the user. The control unit 39 and user interface 21 may be of course implemented by a computer system, such as a personal computer (PC) for example, employing standard processing, memory, input and display, utilities.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A biomedical electrode structure comprising:
    a contact member having a tissue interfacing face for contacting a tissue surface, and an opposite electrical coupling face;
    at least first and second electrically conductive surfaces configured to electrically couple to different first and second portions of the contacted tissue, the first electrically conductive surface being disposed within said tissue interfacing face and the second electrically conductive surface being disposed on the tissue interfacing face and being spaced apart from the first electrically conductive surface;
    at least three electrical connectors comprising at least two electrical connectors mounted in a spaced apart relationship on said electrical coupling face and electrically coupled to different regions of said first electrically conductive surface for allowing measurement of at least one electrical property of at least a portion of said at least first electrically conductive surface residing therebetween; and
    at least one additional electric connector electrically coupled to said second electrically conductive surface and being configured and operable to sense electric signals propagating in the contacted tissue in response to electric signals applied by the at least first electrically conductive surface.

2. The biomedical electrode structure according to claim 1, wherein the at least first electrically conductive surface is an elongated surface, and wherein the at least two electrical connectors are electrically coupled to regions of said first electrically conductive surface to permit measurement of the at least one electrical property along substantial length of the first electrically conductive surface.

3. The biomedical electrode structure according to claim 2, wherein an aspect ratio of the elongated geometry of the first electrically conductive surface is generally in the range of 0.13 to 0.53.

4. The biomedical electrode structure according to claim 2, wherein the length of the first electrically conductive surface is generally in the range of 30 to 60 mm.

5. The biomedical electrode structure according to claim 2, wherein the first electrically conductive surface is of a rectangular shape having a width generally in the range of 8 to 16 mm.

6. The biomedical electrode structure according to claim 1, wherein the at least one electrical property includes electrical impedance, resistance or conductivity.

7. The biomedical electrode according to claim 1, wherein the second electrically conductive surface is an elongated surface.

8. The biomedical electrode structure according to claim 1, wherein the first electrically conductive surface and the second electrically conductive surface are configured such that electrical currents passing in the contacted tissue due to the applied electric signals propagate in a direction substantially perpendicular to at least one of said electrically conductive surfaces.

9. The biomedical electrode structure according to claim 8, wherein the electrically conductive surfaces are disposed on the tissue interfacing surface substantially parallel to each other, such that the electrical currents propagating therebetween are homogenously distributed at least along the length of the contacted tissue.

10. The biomedical electrode structure according to claim 1, wherein the distance between the electrical conductive surfaces is in the range of 30 to 60 mm.

11. A method for calibrating the electrode structure of claim 1 to thereby enable its use in a biomedical monitoring setup, the method comprising:
  (a) applying electrical signals to said first electrically conductive surface via at least one of said at least two electrical connectors;
  (b) measuring responsive electrical signals propagating in said first electrically conductive surface via at least one other of said at least two electrical connectors and generating data indicative of said measured propagating electrical signals; and
  (c) analyzing said data and determining at least one electrical property of said first electrically conductive surface.

12. A method according to claim 11, further comprising:
  (d) issuing an indication whenever the determined at least one electrical property is not acceptable for carrying out the monitoring;
  (e) waiting for replacement of the at least one biomedical electrode; and
  (f) repeating the steps (a) to (e) until determining that the at least one electrical property is acceptable for carrying out the monitoring.

13. A method according to claim 11, further comprising generating calibrating data indicative of the electrical signals to be applied, or of the responsive electrical signals, via said first electrically conductive surface, based on the determined at least one electrical property.

14. A measurement device for monitoring one or more physiological parameters, the device comprising:
  electrical monitoring unit;
  a biomedical electrode structure comprising:
    a contact member having a tissue interfacing face for contacting a tissue surface, and an opposite electrical coupling face;
    at least a first electrically conductive surface disposed within said tissue interfacing face, and being configured to electrically couple to a portion of the contacted tissue; and
    at least two electrical connectors mounted in a spaced apart relationship on said electrical coupling face and electrically coupled to different regions of said first electrically conductive surface for allowing measurement of at least one electrical property of at least a portion of said at least first electrically conductive surface residing therebetween;
  at least one connector configured and operable to electrically couple the electrode structure to the electrical monitoring unit via at least two electrical connectors of said electrode structure;
  a switching circuitry configured and operable to alter connectivity between said electrical monitoring unit and said at least one connector to provide one of the following operating modes:
  a testing mode for measuring at least one electrical property of said electrode structure; and
  a monitoring mode for applying electrical signals from said electrical monitoring unit to a tissue contacted by said electrode structure or for sensing via said electrode structure electrical signals propagating in said tissue.

15. The measurement device according to claim 14, wherein the electrical monitoring unit comprises an electrometer and an electrical signal generator.

16. The measurement device of claim 14, wherein the at least one connector comprises a connector unit for electrically coupling said monitoring unit to said electrode structure comprising two electrical connectors, the connector unit comprising:
  two electrically conductive latching elements shiftable between an engaged and disengaged states;
  a housing configured to receive two electrically conductive wires and electrically couple each of said wires with a respective latching element; and
  two actuators movably attached to said housing, configured and operable to change the states of said latching elements between their engaged and disengaged states.

17. The measurement device according to claim 16, wherein
  the two electrical connectors of the biomedical electrode structure are in a form of electrically conducting studs, and
  the latching elements are configured and operable to embrace said studs in their engaged state.

* * * * *